(12) United States Patent
Vogt et al.

(10) Patent No.: US 6,854,624 B2
(45) Date of Patent: Feb. 15, 2005

(54) METHODS FOR IMPROVING PRODUCT CHASSIS AND PANEL CONTROL DURING FOLDING OF GARMENT

(75) Inventors: Brian R. Vogt, Oshkosh, WI (US); Robert Lee Popp, Hortonville, WI (US); Larry D. Primeau, DePere, WI (US); Jack L. Couillard, Menasha, WI (US); John P. Hillmer, Neenah, WI (US); David A. Maxton, Menasha, WI (US); Kurt G. Krupka, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 95 days.

(21) Appl. No.: 10/164,360

(22) Filed: Jun. 6, 2002

(65) Prior Publication Data

US 2003/0226862 A1 Dec. 11, 2003

(51) Int. Cl.$^7$ ............................................... A41H 33/00
(52) U.S. Cl. ....................................................... 223/37
(58) Field of Search ............................... 223/37; 270/45

(56) References Cited

U.S. PATENT DOCUMENTS

| | | |
|---|---|---|
| 4,940,464 A | 7/1990 | Van Gompel et al. |
| 5,104,116 A | 4/1992 | Pohjola |
| 5,110,403 A | 5/1992 | Ehlert |
| 5,135,522 A | 8/1992 | Fahrenkrug et al. |
| 5,224,405 A * | 7/1993 | Pohjola ........................ 83/24 |
| 5,496,429 A | 3/1996 | Hasse et al. |
| 5,607,537 A | 3/1997 | Johnson et al. |
| 5,643,377 A | 7/1997 | Juergens |
| 5,660,666 A | 8/1997 | Dilnik et al. |
| 5,705,013 A | 1/1998 | Nease et al. |
| 5,759,340 A | 6/1998 | Boothe et al. |
| 5,766,389 A | 6/1998 | Brandon et al. |
| 5,795,433 A | 8/1998 | Niedermeyer |
| 5,818,719 A | 10/1998 | Brandon et al. |
| 6,022,431 A | 2/2000 | Blenke et al. |
| 6,036,805 A | 3/2000 | McNichols |
| 6,113,717 A | 9/2000 | Vogt et al. |
| 6,254,714 B1 | 7/2001 | Niedermeyer |
| 6,352,607 B1 | 3/2002 | Kuen et al. |
| 6,358,350 B1 | 3/2002 | Glaug et al. |
| 6,497,032 B2 * | 12/2002 | Maxton et al. ................ 29/429 |
| 2002/0000291 A1 | 1/2002 | Coenen et al. |
| 2002/0002358 A1 | 1/2002 | Durrance et al. |
| 2002/0003021 A1 | 1/2002 | Maxton et al. .............. 156/199 |
| 2002/0003022 A1 | 1/2002 | Csida et al. |
| 2002/0003024 A1 | 1/2002 | Vogt et al. |
| 2002/0005257 A1 | 1/2002 | Tomsovic et al. |
| 2002/0007773 A1 | 1/2002 | Hietpas et al. |

FOREIGN PATENT DOCUMENTS

| | | |
|---|---|---|
| WO | 00/37009 | 6/2000 |
| WO | 01/87210 | 11/2001 |
| WO | 01/87218 | 11/2001 |
| WO | 01/87561 | 11/2001 |

* cited by examiner

*Primary Examiner*—John J. Calvert
*Assistant Examiner*—James G Smith
(74) *Attorney, Agent, or Firm*—Pauley Petersen & Erickson

(57) ABSTRACT

A method and apparatus for folding garments is suitable for use with garments having discrete mechanical fastening components and suitable for the manufacture of prefastened and refastenable garments. The garments or other discrete articles define leading and trailing halves with opposed side panels. A chassis portion and side panels of the garments can be controlled during folding by providing a three piece vacuum puck design and/or a channeled transfer plate as well as a layer of air under the leading side panels.

23 Claims, 13 Drawing Sheets

METHODS FOR IMPROVING PRODUCT CHASSIS AND PANEL CONTROL DURING FOLDING OF GARMENT

BACKGROUND OF THE INVENTION

The present invention pertains to processes and apparatus for folding garments, and more particularly to processes and apparatus for improving chassis and side panel control during folding.

Garments such as disposable absorbent garments have numerous applications including diapers, training pants, feminine care products, and adult incontinence products. The typical disposable absorbent garment is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes.

One form of disposable absorbent garment is a two-dimensional product that has open sides. Two-dimensional products, such as conventional diapers and some adult incontinence products, are generally flat and provided in an unfastened configuration. These garments have typically included fasteners such as adhesive tape fasteners or hook and loop type fasteners that releasably connect the front and back waist portions to secure the products about the wearer. Two-dimensional products can be easily applied or removed while the wearer is lying down.

Another form of disposable absorbent garment is a three-dimensional product with closed sides so that (using a pant as an example) the product has a unitary waist opening and two leg openings. The wearer raises and lowers the garment to apply the product. Three-dimensional products are particularly appealing because the pant has a very garment-like look. Children, for instance, identify diaper products with babies, and most children do not like being identified with or as babies. Consequently, these children do not want to wear baby diapers, and may instead prefer to wear training pants that look like adult underwear. Thus, the switch from a traditional diaper to a more garment-like or underwear-like training pant can be an important step in the toilet training process. Similarly, adults seeking the protection of incontinence products prefer the normalcy of a pant product rather than an incontinence product that must be applied in another fashion. Three-dimensional garments generally have been designed such that they can be torn to remove the garment from the wearer after it has been soiled. In addition, some three-dimensional garments have been designed with refastenable fasteners.

Disposable absorbent products present many manufacturing challenges. In part, this is due to the high speed that is necessary to economically produce relatively low cost disposable absorbent products. Furthermore, such products must be folded in a manner that allows the front and back of the garment to be properly aligned and joined. An even more precise folding may be required if the garment has fasteners on front and back regions that must be aligned and joined properly in order for the garment to function as desired. By providing a refastenable feature, the product delivers the advantage of being both a pant and easy to change when soiled. The folding of training pants has been previously described in International Publication No. WO 01/87210 published 22 Nov. 2001 by Joseph D. Coenen et al., which is incorporated herein by reference. As described therein, unfolded training pants are guided by a product control drum onto a transfer plate. A pair of tucker blades then contact the crotch region of the training pant, inserting the training pant into a folding nip formed between nose rolls of an upper folding conveyor and a lower folding conveyor in order to effectuate the folding of training pants.

However, folding such training pants can present new challenges for high speed manufacturing. For example, the center chassis portion of such products may sometimes interfere with the nose rolls and transfer plate. This interference may cause alignment problems for the chassis. As another example, when the pant is drawn into the folding nip, the leading edge of the chassis may sometimes become misaligned. Finally, as another example, when the pant is drawn into the folding nip, the side panels of the leading edge of the pant may get out of control and become skewed. This (possibility of skewing) is especially due to the flexibility of the material. There may be a larger probability of skewing when lower basis weight materials are used, and/or at higher machine speeds. The flexibility of the material, while it may cause processing issues, is nevertheless needed to provide maximum conformability of the garment to the body.

Thus, what is lacking and needed in the art are improved processes and apparatus for folding garments to address the above identified problems, which processes and apparatus are suitable for use with discrete articles including mechanical fastening components and suitable for the manufacture of prefastened and refastenable pants.

SUMMARY OF THE INVENTION

In response to the above-referenced unfulfilled need in the art, new processes and apparatus for folding pants have been discovered.

One aspect of the present invention pertains to a method of folding garments. One embodiment of the method includes creating a folding nip between first and second folding conveyors. A plurality of discrete articles are transported toward the folding nip. Each discrete article includes a chassis and defines a leading half including opposed leading side panels, a trailing half including opposed trailing side panels, and an interconnecting region disposed between and interconnecting the leading and trailing halves. The leading half is guided onto a transfer plate by a product control drum including vacuum pucks having multiple pieces, one to support the chassis and two to support the leading side panels. The interconnecting region is moved into the folding nip.

In another embodiment of the method, a plurality of discrete articles are transported toward the folding nip formed between first and second folding conveyors. Each discrete article includes a chassis and defines a leading half including opposed leading side panels, a trailing half including opposed trailing side panels, and an interconnecting region as well as mechanical fastening components. The leading half is guided onto a transfer plate. The transfer plate is channeled and includes two regions which support and control the leading side panels while the second folding conveyor holds the chassis by vacuum. The interconnecting region is moved into the folding nip. The leading and trailing halves are advanced into the folding nip.

Another embodiment of the method of folding garments includes: creating a folding nip between first and second folding conveyors; transporting a plurality of discrete articles on the first folding conveyor, each discrete article including a chassis and defining a leading half including opposed leading side panels, a trailing half including opposed trailing side panels, and an interconnecting region disposed between and interconnecting the leading and trailing halves. The leading half is guided onto a transfer plate which provides a layer of air under the leading side panels by air jets, air knives or air bars. The interconnecting region is moved into the folding nip, and the leading and trailing halves are advanced into the folding nip.

Another aspect of the invention concerns an apparatus for folding garments that include a chassis and have a leading half including opposed leading side panels, a trailing half including opposed trailing side panels, and an interconnecting region disposed between and interconnecting the leading and trailing halves. The apparatus includes first and second folding conveyors defining therebetween a folding nip. The apparatus also includes at least one vacuum puck having three pieces. One of the pieces supports the chassis while the other two pieces support the leading side panels. The apparatus also includes a channeled transfer plate including two regions. The channeled transfer plate allows the second folding conveyer to contact the pants. The transfer plate also provides a layer of air under the leading side panels.

The present invention can be used with garments that include refastenable or non-refastenable seams. Non-refastenable bonded seams can be formed by ultrasonic bonds, adhesive bonds, thermal bonds, sewing, or the like. The present invention provides particular utility with garments that include refastenable seams. Fastening components that form refastenable seams can include separate elements bonded to separate areas of the pant. Alternatively, at least one of the fastening components can include a portion of an element of the garment, such as the bodyside liner, the outer cover, separate side panels if employed, integral side panels if employed, a belt-type component extending transversely across the chassis if employed, or the like. Thus, unless otherwise specified, the term "fastening component" includes separate components which function as fasteners as well as regions of materials such as side panels, liners, outer covers or the like which function as fasteners. Moreover, a single material can define multiple fastening components to the extent that different regions of the material function as separate fasteners. The fastening components can be located on the side panels, between the side panels such as on the absorbent chassis, or a combination of the two. The fastening components can have any desired shape, such as square, rectangular, round, curved, oval, irregularly shaped, or the like. Each fastening component can include a single fastening element or multiple fastening elements.

The fastening components can include any refastenable fasteners suitable for absorbent articles, such as adhesive fasteners, cohesive fasteners, mechanical fasteners, or the like. In particular embodiments the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components include hook-and-loop fastening elements. One skilled in the art will recognize that the shape, density and polymer composition of the hooks and loops may be selected to obtain the desired level of securement between the fastening components and the mating fastening components. A more aggressive hook material may include a material with a greater average hook height, a greater percentage of directionally-aligned hooks, or a more aggressive hook shape.

Refastenable fastening systems allow for easy inspection of the interior of the pant-like product. If necessary, the fastening system also allows the pant to be removed quickly and easily. This is particularly beneficial when the pant contains messy excrement. For training pants, the caregiver can completely remove the pant-like product and replace it with a new one without having to remove the child's shoes and clothing.

The present invention can be used in the manufacture of a wide variety of absorbent and non-absorbent products, including training pants, swim pants, diaper pants, incontinence garments, feminine care products, health care garments, apparel for institutional, industrial and consumer use, or other garments. Absorbent articles are adapted to be worn adjacent to the body of a wearer to absorb and contain various exudates discharged from the body. The absorbent articles can be prefastened to provide a pant-like product for the user. The product can then be pulled on like a conventional training pant or undergarment, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

Particular training pants suitable for use with the present invention are disclosed in U.S. patent application Ser. No. 09/444,083, filed on Nov. 22, 1999 (corresponding to PCT application WO 00/37009 published Jun. 29, 2000) by A. Fletcher et al. and titled "Absorbent Articles With Refastenable Side Seams," which is incorporated herein by reference. This reference describes various materials and methods for constructing training pants. Training pants can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; which are also incorporated herein by reference.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The methods and apparatus of the present invention can be used to fold a variety of garments. Examples of such garments include disposable absorbent articles such as diapers, training pants, feminine hygiene products, incontinence products, other personal care or health care garments, swim pants, athletic clothing, pants and shorts, or the like. For ease of explanation, the description hereafter will be in terms of methods and apparatus for making and folding a child's training pant. In particular, the methods and apparatus will be described in terms of those for making prefastened disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference.

Figure 1:
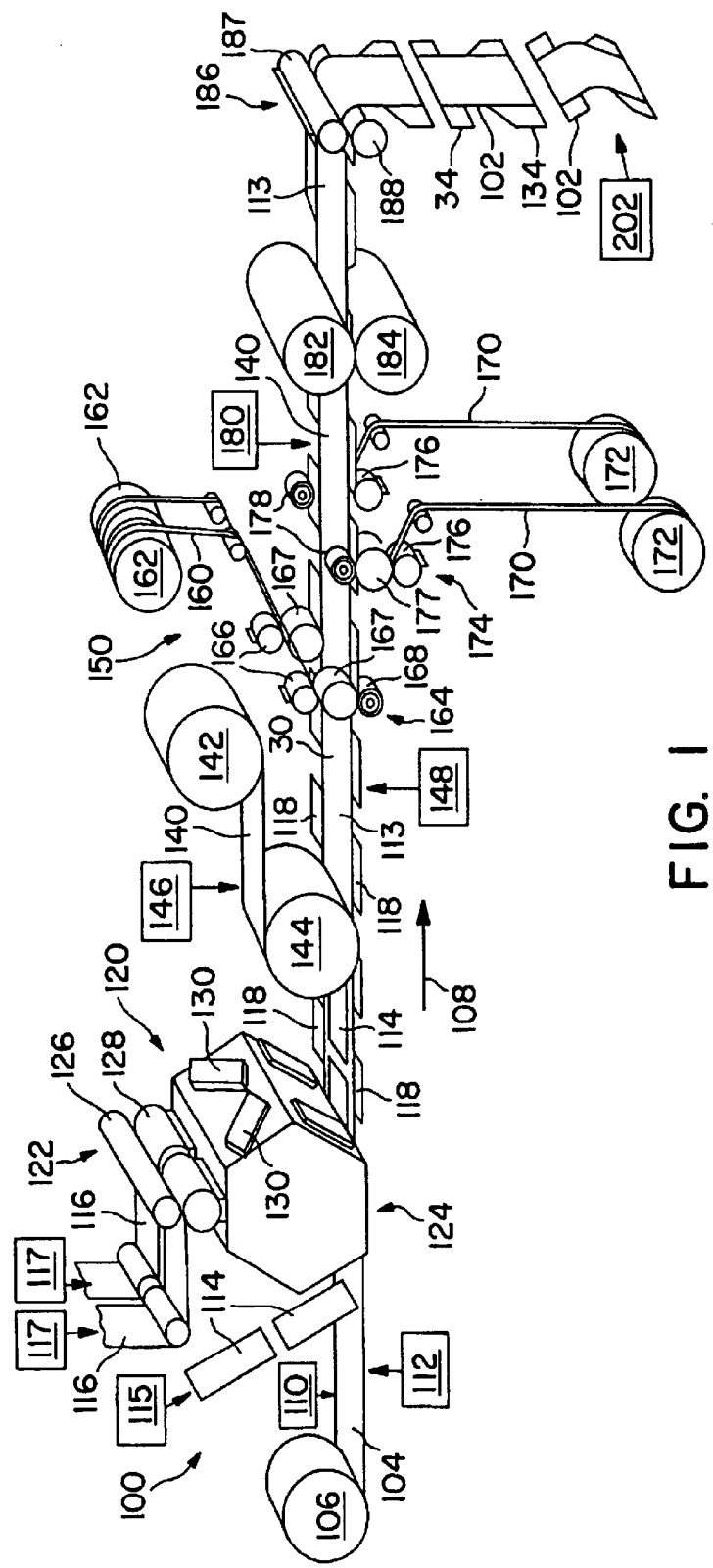
FIG. 1 is a schematic view of an exemplary embodiment of an assembly section for making garments such as training pants.

FIG. 1 representatively illustrates one embodiment of a method and apparatus for making a training pant 20, represented as garment 102. The training pant 20 is illustrated separately and in a partially fastened condition in FIG. 4. The training pant 20 includes an absorbent chassis 32 and a fastening system 80. The absorbent chassis 32 defines a front waist region 22, a back waist region 24, a crotch or interconnecting region 26 interconnecting the front and back waist regions, an inner surface 28 which is configured to contact the wearer, and an outer surface 30 opposite the inner surface which is configured to contact the wearer's clothing. With additional reference to FIGS. 5 and 6, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 4:
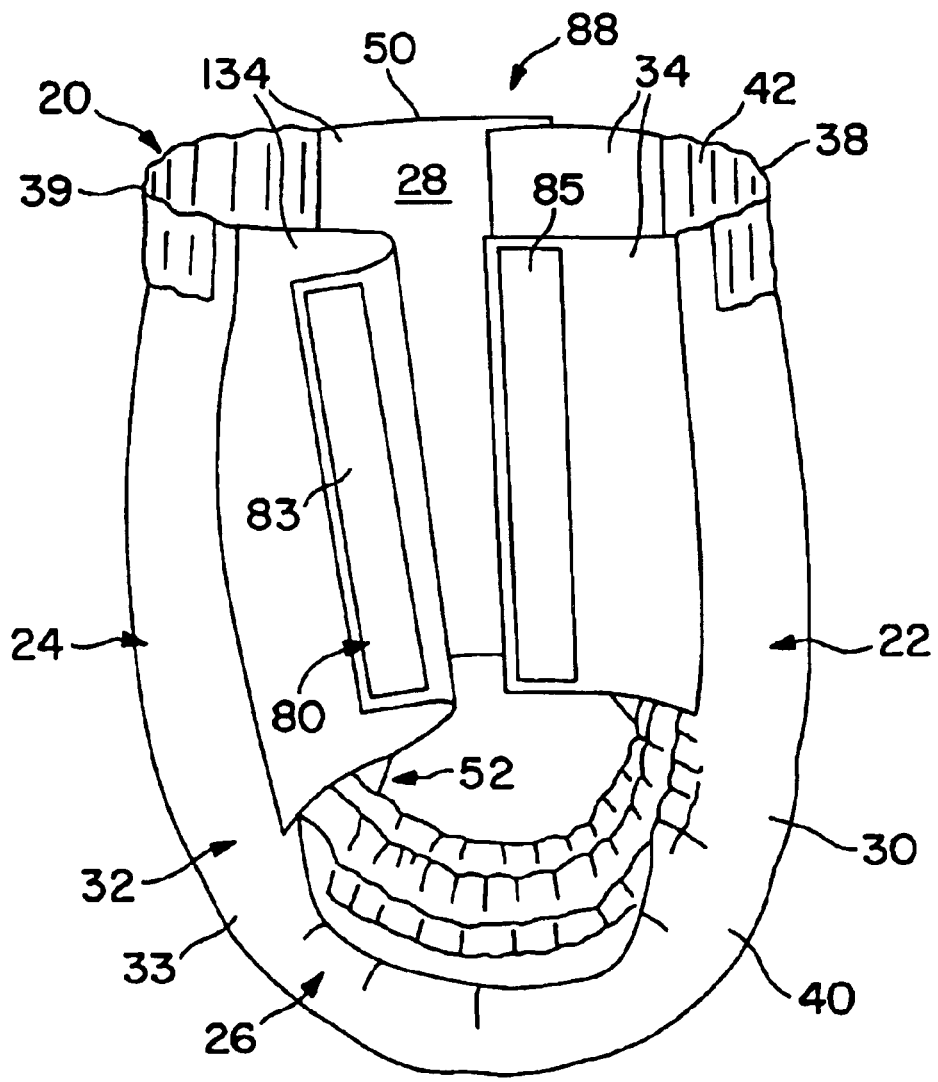
FIG. 4 illustrates a side view of a training pant made by the process and apparatus shown in FIG. 1, where the fastening system is shown engaged on one side of the training pant and disengaged on the other side of the training pant.
Figure 5:
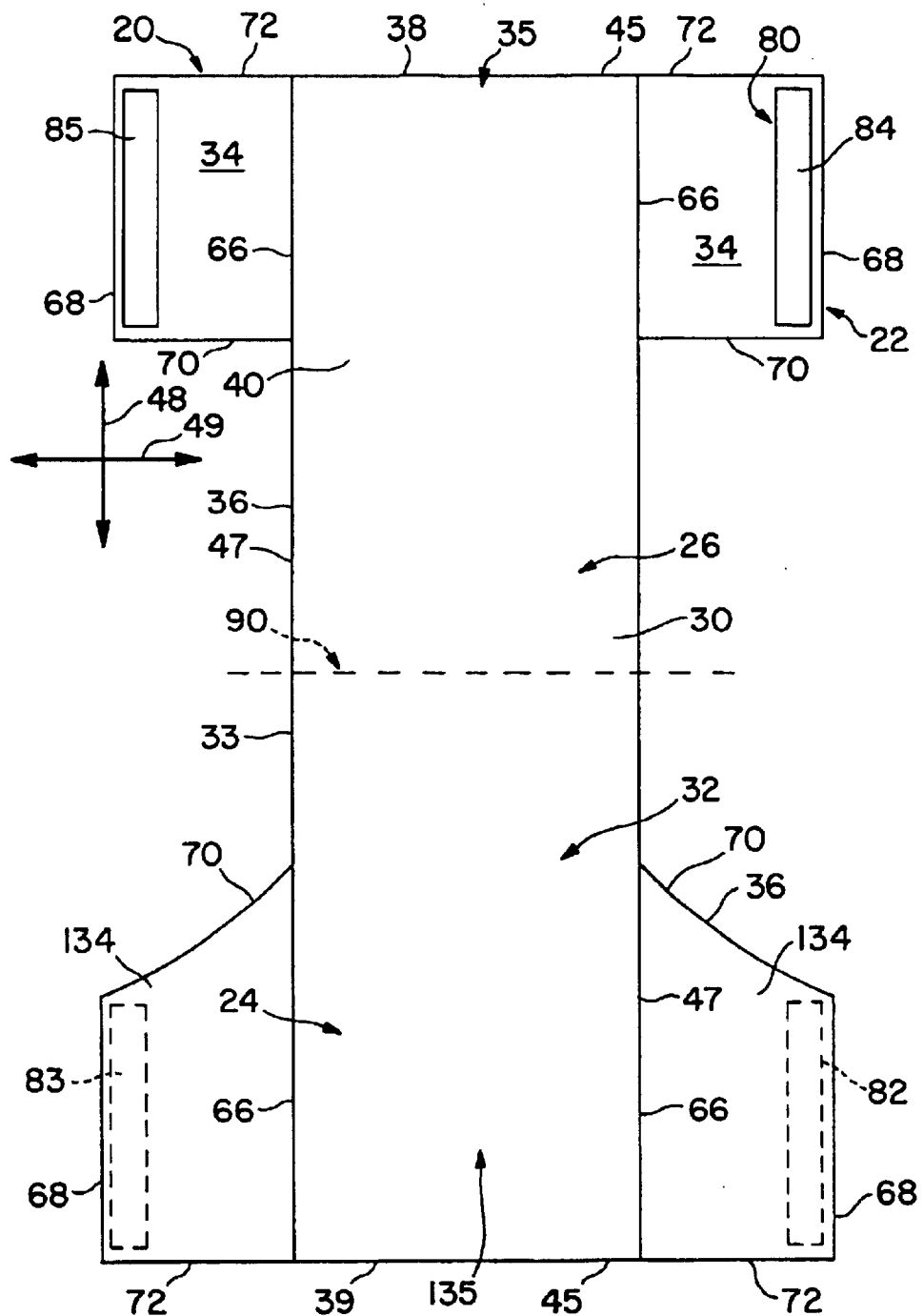
FIG. 5 illustrates a plan view of the training pant shown in FIG. 4 in an unfastened, stretched and laid flat condition, and showing the surface of the training pant that faces away from the wearer.
Figure 6:
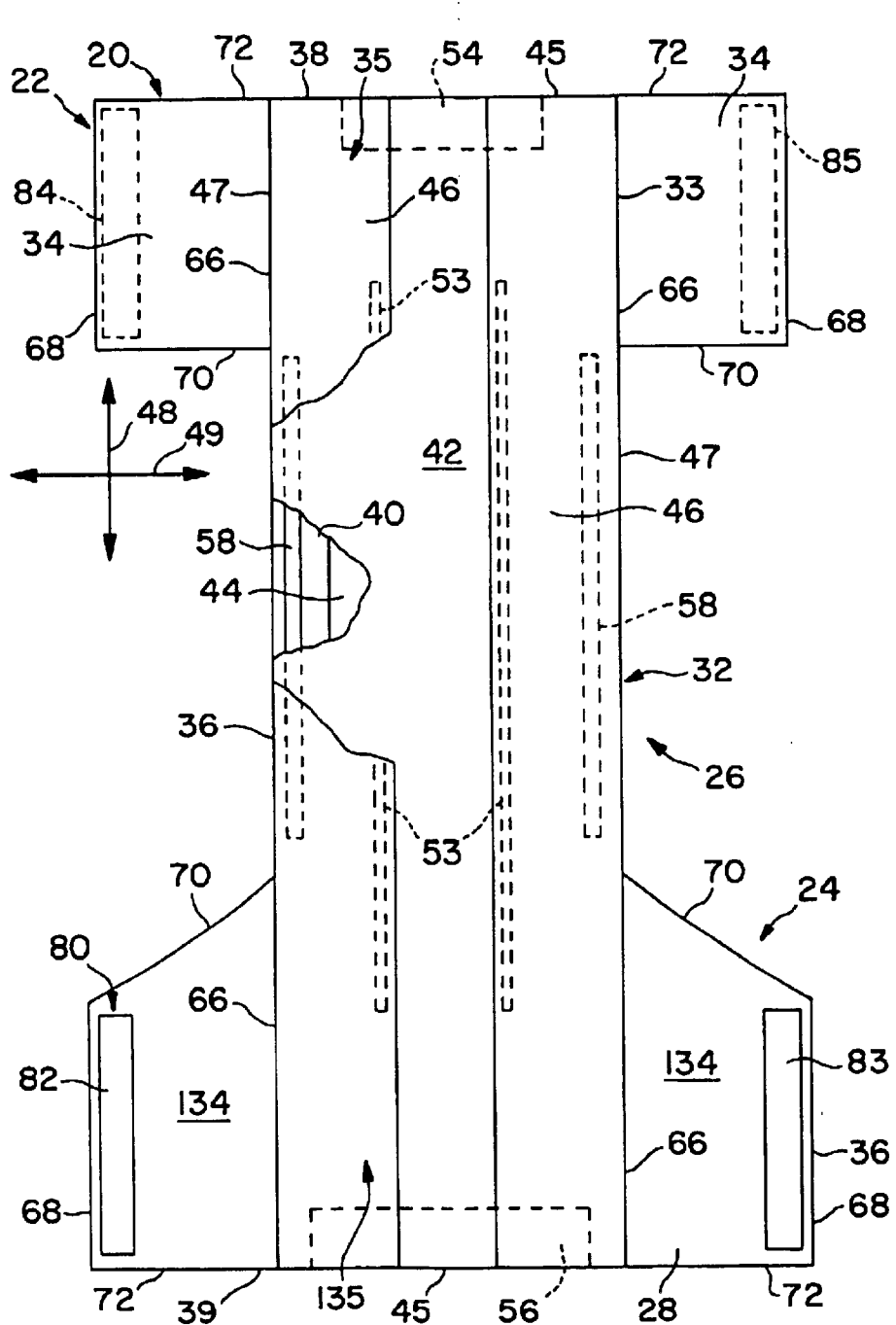
FIG. 6 illustrates a plan view similar to FIG. 5, but showing the surface of the training pant that faces the wearer when the training pant is worn, and with portions cut away to show the underlying features.

The illustrated absorbent chassis 32 includes a composite structure 33 which can be rectangular or any other desired shape, a pair of transversely opposed front side panels 34, and a pair of transversely opposed back side panels 134. The composite structure 33 and side panels 34 and 134 may include two or more separate elements, as shown in FIG. 4, or may be integrally formed. Integrally formed side panels and composite structure would include at least some common materials, such as the bodyside liner, flap composite, outer cover, other materials and/or combinations thereof, and could define a one-piece elastic, stretchable, or non-stretchable pant. The illustrated composite structure 33 includes an outer cover 40, a bodyside liner 42 (FIGS. 4 and 6) which is connected to the outer cover in a superposed relation, an absorbent assembly 44 (FIG. 6) which is located between the outer cover and the bodyside liner, and a pair of containment flaps 46 (FIG. 6). The illustrated composite structure 33 has opposite linear end edges 45 that form portions of the front and back waist edges 38 and 39, and opposite linear or curvilinear side edges 47 that form portions of the side edges 36 of the absorbent chassis 32 (FIGS. 5 and 6). For reference, arrows 48 and 49 depicting the orientation of the longitudinal axis and the transverse axis, respectively, of the training pant 20 are illustrated in FIGS. 5 and 6.

With the training pant 20 in the fastened position as partially illustrated in FIG. 4, the front and back waist regions 22 and 24 are joined together to define a three-dimensional pant configuration having a waist opening 50 and a pair of leg openings 52. The front waist region 22 includes the portion of the training pant 20 which, when worn, is positioned on the front of the wearer while the back waist region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front waist region 22 of the absorbent chassis 32 includes the transversely opposed front side panels 34 and a front center panel 35 (FIGS. 5 and 6) positioned between and interconnecting the side panels. The back waist region 24 of the absorbent chassis 32 includes the transversely opposed back side panels 134 and a back center panel 135 (FIGS. 5 and 6) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 6) can be operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art.

To further enhance containment and/or absorption of body exudates, the training pant 20 desirably although not necessarily includes a front waist elastic member 54, a rear waist elastic member 56, and leg elastic members 58, as are known to those skilled in the art (FIG. 6). The waist elastic members 54 and 56 can be operatively joined to the outer cover 40 and/or bodyside liner 42 along the opposite waist edges 38 and 39, and can extend over part or all of the waist edges. The leg elastic members 58 can be operatively joined to the outer cover 40 and/or bodyside liner 42 along the opposite side edges 36 and positioned in the crotch region 26 of the training pant 20. The leg elastic members 58 can be longitudinally aligned along each side edge 47 of the composite structure 33.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. Du Pont de Nemours and Company, Wilmington, Del. U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from Uniqema Inc., a division of ICI of New Castle, Del., U.S.A. and GLUCOPON® 220UP available from Cognis Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/ polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pant can include elastomeric or nonelastomeric materials.

The absorbent assembly 44 (FIG. 6) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 which can be rectangular or any other desired shape includes a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis, 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown).

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 5 and 6, the front side panels 34 can be permanently bonded to and extend transversely beyond the side edges 47 of the composite structure 33 in the front waist region 22, and the back side panels 134 can be permanently bonded to and extend transversely beyond the side edges 47 of the composite structure in the back waist region 24. The side panels 34 and 134 may be attached using attachment means known to those skilled in the art such as adhesive, thermal or ultrasonic bonding. Alternatively, the side panels 34 and 134 can be formed as an integral portion of a component of the composite structure 33. For example, the side panels can include a generally wider portion of the outer cover, the bodyside liner, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the illustrated back side panels 134 have a continually decreasing length dimension moving from the attachment line 66 to the distal edge 68, as is best shown in FIGS. 5 and 6.

The side panels 34 and 134 desirably although not necessarily include an elastic material capable of stretching in a direction generally parallel to the transverse axis 49 of the training pant 20. Suitable elastic materials, as well as processes of incorporating elastic side panels into a training pant, are known to those skilled in the art and are described for example in U.S. Pat. No. 4,940,464 issued Jul. 10, 1990 to Van Gompel et al., of which is incorporated herein by reference.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 includes a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each include hook type fasteners and the second fastening components 84 and 85 each include complementary loop type fasteners. In another particular embodiment, the first fastening components 82 and 83 each include loop type fasteners and the second fastening components 84 and 85 each include complementary hook type fasteners. Alternatively, the fastening components can include interlocking similar surface fasteners; adhesive or cohesive fastening elements such as an adhesive fastener and an adhesive-receptive landing zone or material; or the like. Although the illustrated embodiments show the back waist region 24 overlapping the front waist region 22, which is convenient, the training pant 20 can also be configured so that the front waist region 22 overlaps the back waist region 24.

Loop type fasteners typically include a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding or needle punching. Loop type materials can also include any fibrous structure capable of entangling or catching hook type materials, such as carded, spunbonded or other nonwoven webs or composites, including elastomeric and nonelastomeric composites, in addition to knitted or woven materials. Suitable loop materials are available from Guilford Mills, Inc., Greensboro, N.C., U.S.A.

Hook type fasteners typically include a fabric or material having a base or backing structure and a plurality of hook members extending upwardly from at least one surface of the backing structure. Suitable hook material can be molded or extruded of nylon, polypropylene, polyethylene, or another suitable material. Suitable single-sided hook materials for the fastening components 82–85 are available from commercial vendors such as Velcro Industries B.V., Amsterdam, Netherlands or affiliates thereof.

With particular reference to FIG. 6, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 5, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 include loop type fasteners disposed on the inner surface 28 and the second fastening components 84 and 85 include hook type fasteners disposed on the outer surface 30, the first fastening components can be sized larger than the second fastening components to ensure coverage of the rigid, outwardly-directed hooks.

The fastening components 82–85 can be adhered to the side panels 34 and 134 by any means known to those skilled in the art such as adhesive bonds, ultrasonic bonds or thermal bonds. The fastening components can include separate fastening elements or can include distinct regions of an integral material. For example, the training pant 20 can include an integral second fastening material disposed in the front waist region 22 for refastenably connecting to the first fastening components 82 and 83 at two or more different regions, with the integral second fastening material defining the second fastening components 84 and 85 (FIG. 5). In a particular embodiment, the fastening components can include integral portions of the waist regions. For instance, one of the elastomeric front or back side panels can function as second fastening components in that they can include a material that is releasably engageable with fastening components disposed in the opposite waist region.

The fastening components are desirably rectangular, although they may alternatively be square, round, oval, curved or otherwise non-rectangularly shaped. In particular embodiments, it may be desirable for one or more of the fastening components to include a plurality of relatively smaller fastening elements.

When the fastening components 82–85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it can be desirable in some embodiments for the front side panels 34 to be longitudinally spaced from the back side panels 134 (see FIGS. 5 and 6). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82–85 form refastenable seams 88 (FIG. 4) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82–85 can be formed to cover about 80 to 100 percent, and more particularly about 90 to about 98 percent, of the distance between the waist end edge 70 and the leg end edge 72 of the side panels 34 and 134. In other embodiments, the fastening components can include a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it can be particularly desirable for the transverse distance between the first fastening components 82 and 83 to be substantially equal to the transverse distance between the second fastening components 84 and 85. In the alternative, the traverse distance between the first fastening components 82 and 83 may be less than or greater than the traverse distance between the second gastening components 84 and 85. The transverse distance between a set of fasteners is measured parallel to the transverse axis 49 between the longitudinal center lines of the fasteners, measured with the side panels 34 and 134 in an unstretched condition.

An exemplary embodiment of an assembly section 100 for making a continuous stream of partially assembled, discrete training pants or garments 102 is illustrated in FIG. 1. The specific equipment and processes used in the assembly section 100 can vary greatly depending on the specific type of garment being manufactured. The particular process and apparatus described in relation to FIG. 1 is specifically adapted to manufacture training pants 20 of the type illustrated in FIG. 4.

The various components of the garment 102 can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIGS. 1 and 2. Suitable absorbent supply mechanisms, web unwinds, conveyor systems, registration systems, drives systems, control systems and the like, for use with the present process are disclosed in U.S. Pat. No. 5,766,389 issued Jun. 16, 1998 to Brandon et al., which is incorporated herein by reference.

A continuous supply of material 104 used to form the bodyside liner 42 is provided from a supply source 106. The supply source 106 can include for example any standard unwind mechanism, which generally includes a pair of spindles, a festoon assembly, and a dancer roll for providing bodyside liner material 104 at a desired speed and tension.

Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can include either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The product assemblage 113 will be cut downstream to form the partially assembled, discrete garments 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each training pant. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can include one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 1 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive garments 102.

One suitable applicator device 120 is disclosed in U.S. Pat. Nos. 5,104,116 issued Apr. 14, 1992 and 5,224,405 issued Jul. 6, 1993 both to Pohjola, which are incorporated herein by reference. The applicator device 120 can include a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can include a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34 and 134 of the training pant 20 can be provided by portions of the bodyside liner 42 and/or outer cover 40.

A continuous supply of material 140 used to form the outer cover 40 can be provided from a supply roll 142 or other suitable source. The outer cover material 140 can be transported over a laminator roll 144 and married with the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream of the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A. The bonding devices 148 could otherwise be a thermal or adhesive bonder as are well known.

The continuously moving product assemblage 113 next advances to a fastener application station 150 where fastening components 82–85 are bonded to the strips 118 of side panel material 116. The location of the fastening components on the composite is a function in part of the configuration of the assembly section 100. The illustrated assembly section 100 is configured so that the upwardly facing surface of the product assemblage 113 will become the outer surface 30 of the training pant 20 and the downwardly facing surface will become the inner surface 28. Moreover, the illustrated assembly section 100 is configured to produce partially assembled garments 102 having the front waist region 22 of a leading garment connected to the back waist region 24 of a trailing garment. The process could alternatively employ any combination of different orientations. For example, the upwardly facing surface of the product assemblage could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly section 100 could be constructed as a cross-machine direction process wherein the longitudinal axis 48 of each garment could be perpendicular to the machine direction 108 during part or all of the assembly process.

Figure 7:
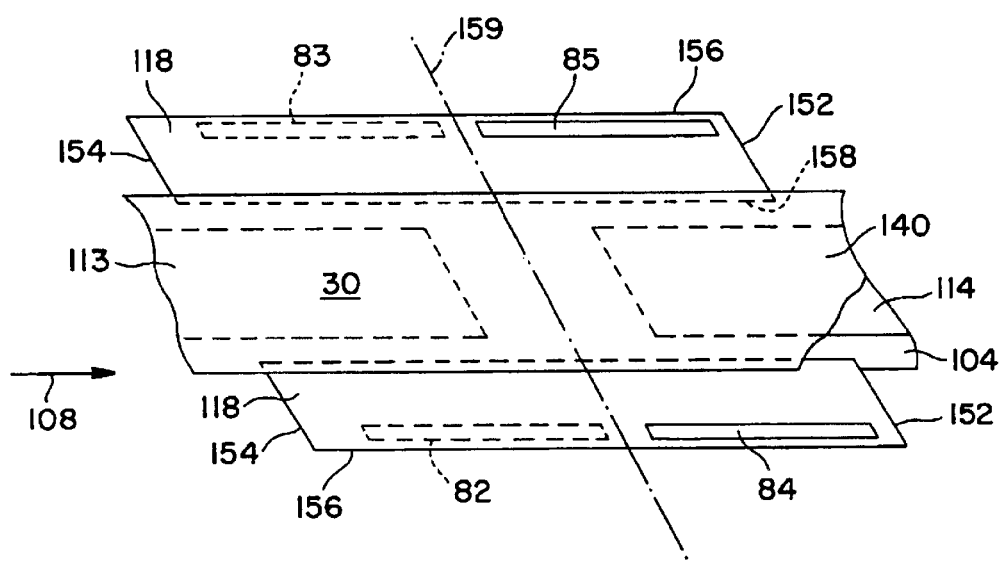
FIG. 7 illustrates a portion of a continuously moving assemblage at one point in the assembly section illustrated in FIG. 1.

The location of the fastening components 82–85 in this embodiment is best illustrated in FIG. 7, which shows a portion of the product assemblage 113 which is moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete garments 102. Based on the illustrated orientation of the continuously moving product assemblage 113, the first fastening components 82 and 83 can be bonded to the underside of the strips 118 and the second fastening components 84 and 85 can be bonded to the top of the strips. Additionally, the first fastening components 82 and 83 can be disposed relatively closer to the trailing edge 154 and the second fastening components 84 and 85 can be disposed relatively closer to the leading edge 152. The first fastening components 82 and 83 can be spaced in the machine direction 108 from the second fastening components 84 and 85 so that the cut line 159 passes therebetween.

With reference again to FIG. 1, continuous webs of second fastener material 160 used to form the second fastening components 84 and 85 (FIGS. 5 and 6) can be provided from supply rolls 162 or other suitable sources. The second fastener materials 160 can be cut into individual second fasteners 84 and 85 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 and 83, shown in FIGS. 5 and 6, can be provided from supply rolls 172 or other suitable sources. The first fastener materials 170 can be cut into individual first fasteners 82 and 83 by cutting assemblies 174 or other suitable devices.

Alternatively, a component of the garment 102 may serve as the first or second fastening component, in which case the fastener application station 150 or the cutting assemblies 174 may not be needed. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

Other arrangements can be used to attach the fastening components 82–85. For example, the fastening components can be applied to the side panel material 116 prior to uniting the side panel material with the bodyside liner material 104 and/or the outer cover material 140; the fastening components can be applied to the bodyside liner material 104 and/or outer cover material 140, whether separate side panels are used or not; portions of other components such as the bodyside liner and/or outer cover can form one or more of the fastening components; the separate side panels or integral side panels can themselves form one or more of the fastening components; the fastening components can be attached as pre-engaged composites 82, 84 and 83, 85; or the like.

After the fastening components are disposed on the strips 118 of side panel material 116, bonding devices 180 such as ultrasonic bonders can be employed to bond the fastening components to the strips. For example, the strips 118 can be transported between a rotary ultrasonic horn and an anvil roll, which devices are positioned on each side of the process at the cross machine direction location of the fastening components 82, 84 and 83, 85. Particular ultrasonic bond patterns including individual, circular bonds which are compatible with mechanical fastening materials are disclosed in U.S. Pat. No. 5,660,666 issued Aug. 26, 1997 to Dilnik et al., which is incorporated herein by reference. Efficient arrangements for attaching the fastening components with nonadhesive bonding devices are further described in U.S. patent application Ser. No. 09/855,484, filed on May 15, 2001 (U.S. Publication US 2002/0000291, Jan. 3, 2002) by J. D. Coenen et al. and titled "Methods For Making Garments With Fastening Components," which is incorporated herein by reference. For secure attachment, it may be desirable to attach the fastening components with both adhesive and thermal bonds. Suitable attachment adhesives are available from commercial vendors such as Findley Adhesive, Inc., Wauwatosa, Wis. U.S.A.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82–85 and the side panel material 116 when the side panel material 116 reaches a particular machine direction 108 location. In one particular embodiment, the target areas correspond to portions of the fastening components 82–85 near the waist edges 38 and 39. The bonding devices 180 can be registered to provide a relatively higher degree of bonding which begins while disposed on one fastening component (such as 84 in FIG. 7), continues through the region where the product assemblage 113 will subsequently be cut (see cut line 159 in FIG. 7), and ends after being disposed on another fastening component (such as 82). Alternatively, the bonding devices 180 can destroy engaging elements of the fastening components 82–85 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 5 and 6). To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

Figure 2:
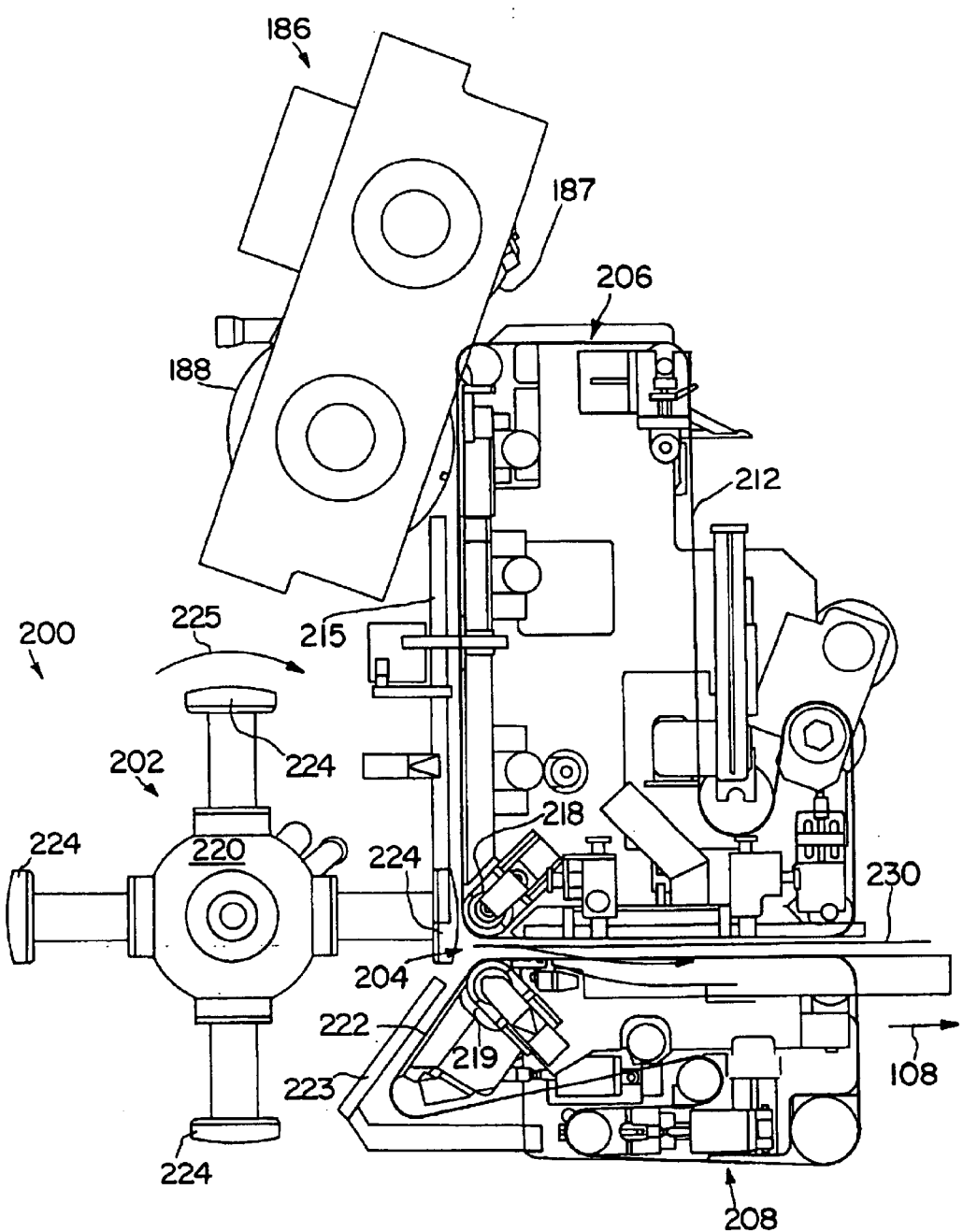
FIG. 2 is a schematic side view of one embodiment of a method and apparatus for folding garments according to the present invention, the view illustrating a folding section which follows the assembly section shown in FIG. 1.

The method and apparatus to this point provides a continuous web of interconnected and partially assembled training pants moving in the direction indicated by arrow 108 (FIG. 7). This continuously moving product assemblage 113 is passed through a cutter 186 (FIG. 2) which selectively cuts the web into discrete, partially assembled garments 102. Such cutters 186 are generally known to those skilled in the art and can include, for example, the combination of a cutting roll 187 and an anvil roll 188 through which the web travels (FIG. 2). The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

Figure 8:
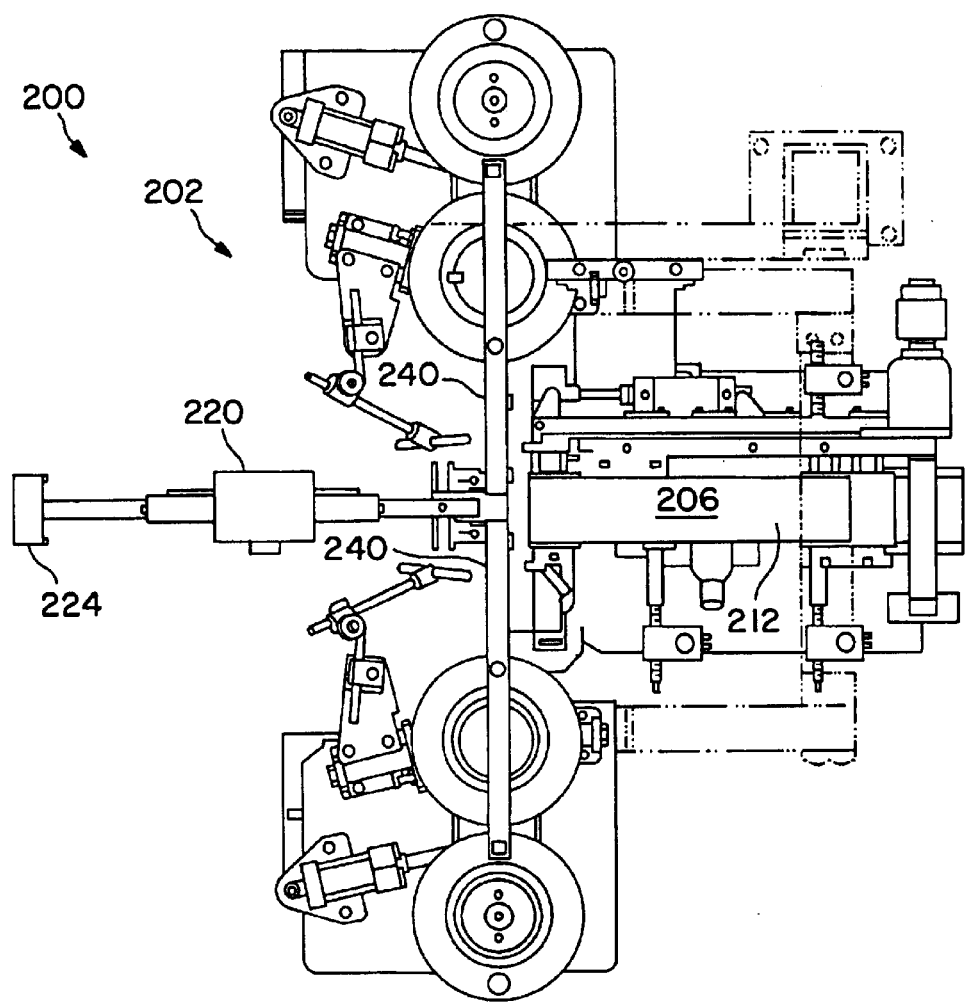
FIG. 8 illustrates a top view of a portion of the folding section shown in FIG. 2.
Figure 10:
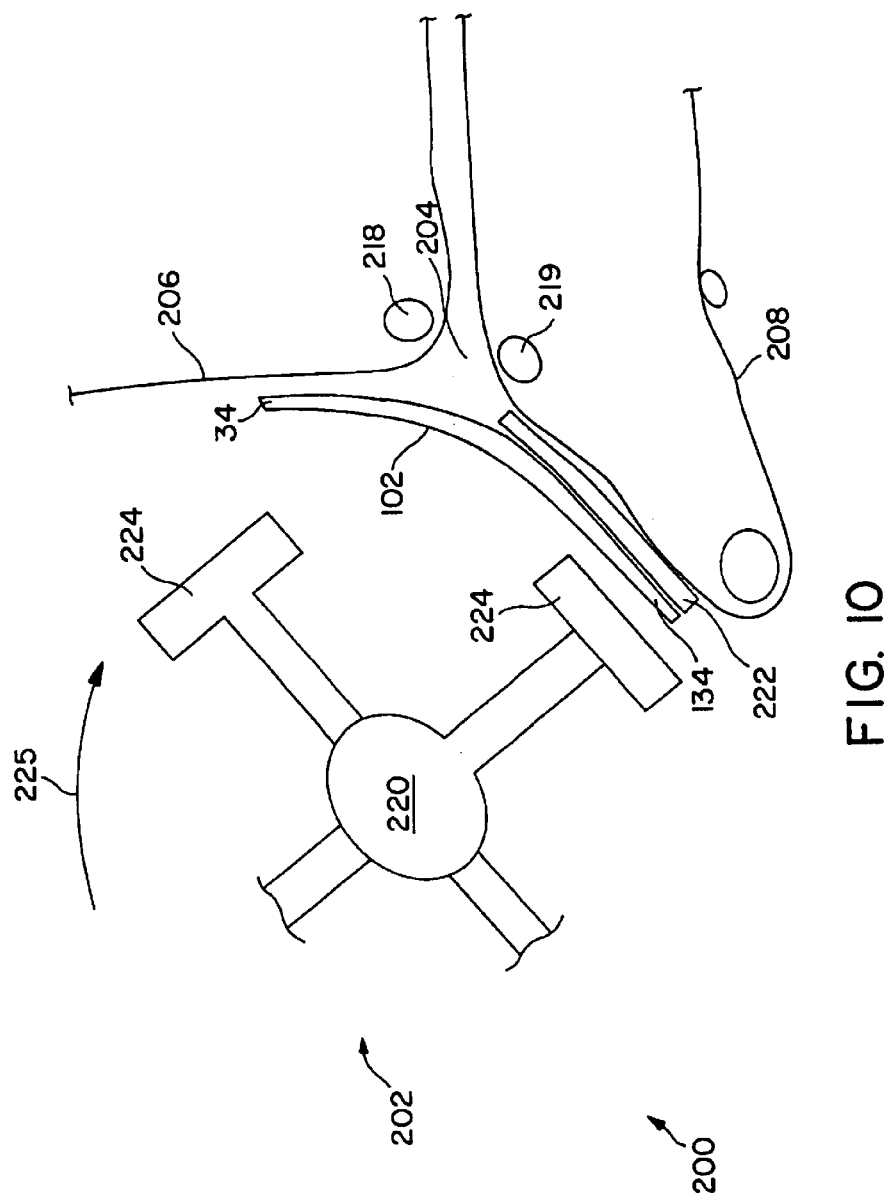
FIG. 10 is a schematic enlarged side view of the folding section shown in FIG. 2.
Figure 11:
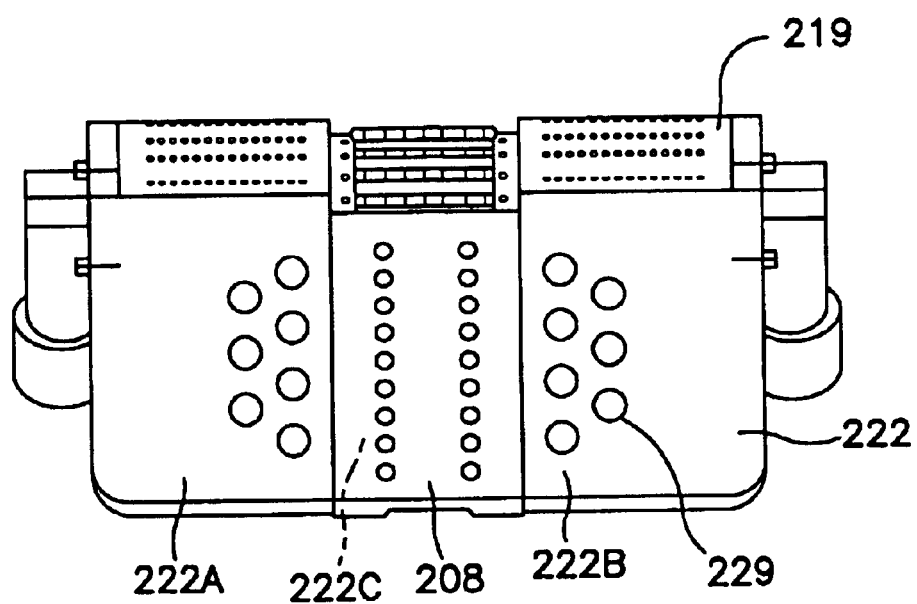
FIG. 11 is an enlarged front view of the apparatus for folding garments according to the present invention showing the channeled transfer plate.

The discrete garments 102 can then be folded using the methods and apparatus according to the present invention. One embodiment of a folding station 200 including a blade folding mechanism 202 according to the present invention and adapted for use with garments incorporating refastenable fastening components 82–85 is illustrated in FIGS. 2, 8 and 10. The illustrated folding mechanism 202 controls the side panels 34 and 134 during folding so that the refastenable fastening components 82–85 are unlikely to engage one another or engage another material during the folding operation. The garments 102 can be folded about a fold line 90 (FIGS. 5 and 12) generally bisecting the garments. As such, the waist regions 22 and 24 of each garment 102 are positioned in facing relationship with the side panels 34 and 134 extending laterally outward relative to the longitudinal axis 48 of the training pant. The fold line 90 can extend in a lateral direction through the crotch region 26 of the training pant Desirably, each discrete garment 102 is consistently folded about the fold line 90 such that the front and back waist edges 38 and 39 of the training pant align with each other.

The illustrated folding mechanism 202 includes a plurality of rotating folding or tucker blades 240 (FIG. 8) which are configured to contact the garment 102 along the fold line 90. Rotation of the folding blades 240 can force the garment 102 into a folding nip 204 (FIG. 2) between two rotating folding conveyors 206 and 208 causing the training pants to fold about the fold line 90. The folding conveyors 206 and 208 can form part of a transport system for moving the folded garments 102 in the machine direction 108 (FIG. 2). The folded garments 102 are transported in the machine direction 108 with the crotch region 26 leading the waist regions 22 and 24. Alternatively, the process and apparatus could be modified so that the waist regions lead the crotch region (not shown).

With reference to FIGS. 2 and 8, the series of unfolded, discrete garments 102 can be transferred from the vacuum anvil roll 188 of the cutter 186 to the upper folding conveyor 206. The garments 102 can be held by vacuum on the upper folding conveyor 206 and transported toward the folding nip 204 formed between the folding conveyors 206 and 208. While being transported toward the folding nip 204, the side panels 34 and 134 can be smoothed out or straightened if desired by various means including fluid stabilizing devices. For example, air bars 215 (FIG. 2), air knives, air nozzles or the like can be mounted in proximity to the upper folding conveyor 206 to provide a stream of fluid directed toward the side panels 34 and 134 to stabilize and/or straighten the side panels. The air bars 215 can blow the side panels 34 and 134 against skid plates (not shown) positioned transversely outward from the upper folding conveyor belt 212. Alternatively, or in addition thereto, the upper folding conveyor 206 can incorporate fluid stabilizing devices consisting of fluid manifolds operatively connected to a high pressure fluid source to fluidly shake the side panels. The fluid stabilizing devices desirably prevent folding of the side panels 34 and 134 as the garment 102 moves along the upper folding conveyor 206. In the alternative, a wide, non-vacuum upper folding conveyor 206, or a belt with vacuum only in the center portion for the chassis could be used.

The product folding nip 204 can be formed between a nose roll 218 of the upper folding conveyor 206 and a nose roll 219 of the lower folding conveyor 208 (FIG. 2). One or both of the nose rolls 218 and 219 desirably although not necessarily include timed vacuum rolls. As the leading edge of a garment 102 is introduced onto the upper nose roll 218, compressed air can be introduced inside the nose roll to negate vacuum draw of the upper nose roll 218. This allows the leading edge of the pant to be transported past the nose roll 218 and the folding nip 204 without getting sucked into the folding nip 204. Alternatively, the vacuum source can be temporarily disconnected from the nose roll 218. Any suitable control system can be used to repeatedly activate and deactivate vacuum operation of the nose rolls 218 and 219. In particular embodiments, rotary valves can be employed to cycle pressure and/or vacuum at the surfaces of the nose rolls 218 and 219.

A product control drum 220 can guide the leading half of the garment 102 onto a transfer plate 222 (FIGS. 2 and 10). The product control drum 220 can include any number of vacuum pucks 224 which rotate in the direction of arrow 225 (FIGS. 2 and 10). The illustrated product control drum 220 includes four vacuum pucks 224 to guide four garments 102 per revolution.

Figure 9:
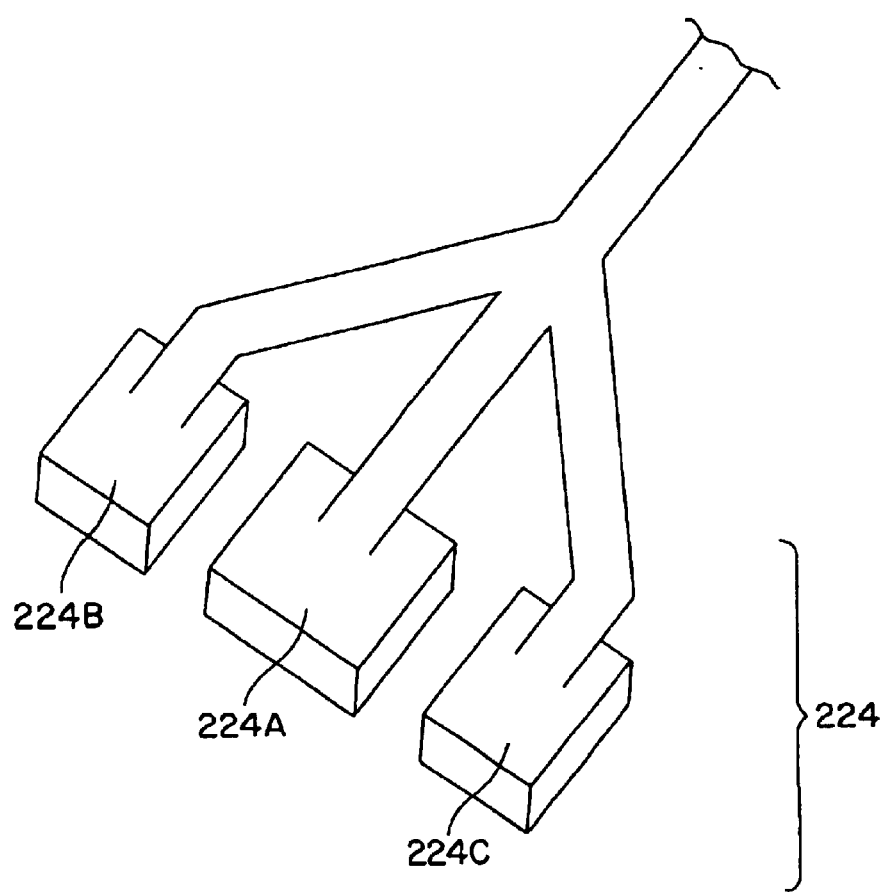
FIG. 9 is a perspective view of the three piece vacuum puck design of the present invention.

According to the invention, as shown in FIG. 9, each vacuum puck 224 includes three pieces 224A, 224B and 224C. Center piece 224A supports the chassis 32 while the two end pieces 224B and 224C support the side panels 134. Each of the vacuum pucks 224 has its own vacuum control. However, pieces 224A, 224B and 224C are all turned on or off together. The amount of vacuum pulled from each piece 224A–C can be varied and controlled seperately by using inserts or blank plates to vary the vacuum to 224, 224B and 224C. This three piece puck design prevents fluttering and skewing of the side panels 134 while the garment 102 is on the product control drum 220.

For example, using the three piece puck design, it is possible, if desired, to provide fluid streams such as from air bars 215 to guide the side panels 34, 134 outward from the upper folding conveyor 206, upstream of the folding nip 204. In addition, it is possible, if desired, to provide fluid streams such as from air bars 223 to continue guiding and controlling the side panels 134 of the leading half of the garment 102 downstream of folding nip 204, while over the transfer plate 222. The air bars 215 and 223 can be located adjacent the outboard edges of upper and lower folding conveyors 206 and 208, directing air generally towards the side panels 34, 134 of garment 102, and generally away from the edges of the upper and lower folding conveyors 206 and 208. The air bars 215 and 223 can additionally be displaced from the planes of the upper and lower folding conveyors 206, 208 so that the garment 102 can pass between the air bars 215, 223 and the conveyors 206 or 208. The air bars 223 can further be aligned with gaps between the vacuum puck pieces 224A–C, so that as the product control drum 220 rotates, the vacuum puck pieces 224A–C pass around the air bars 223 without colliding. Alternatively, if air bars are not employed, a single wide puck 224 may be used to control the product chassis and side panels together. Instead of air bars, airjets or air knives may be used alternatively.

Rotation of the product control drum 220 can be timed so that the vacuum puck 224 grabs the leading half of a garment 102 and transfers the leading edge onto the transfer plate 222. The absorbent chassis 32 and/or side panels 134 of the leading half can be carried on the vacuum puck 224 past the nose roll 219 of the lower folding conveyor 208. Compressed air can be introduced inside this lower nose roll 219 while the side panels 134 are transferred past the nose roll 219 to negate vacuum draw and permit the entire leading edge and side panels 134 to transfer onto the transfer plate 222 (FIG. 10). Alternatively, the vacuum source can be temporarily disconnected from the nose roll 219.

The product control drum 220 generally positions the garments 102 across the folding nip 204, with the leading half and the outstretched leading side panels 134 in proximity to the lower nose roll 219 and the trailing half and the outstretched trailing side panels 34 in proximity to the upper nose roll 218. The leading and trailing halves could alternatively be positioned in proximity to the nose rolls 218 and 219 by depositing the leading and trailing halves over the folding nip 204 rather than running the leading half initially past the folding nip 204.

Figure 12:
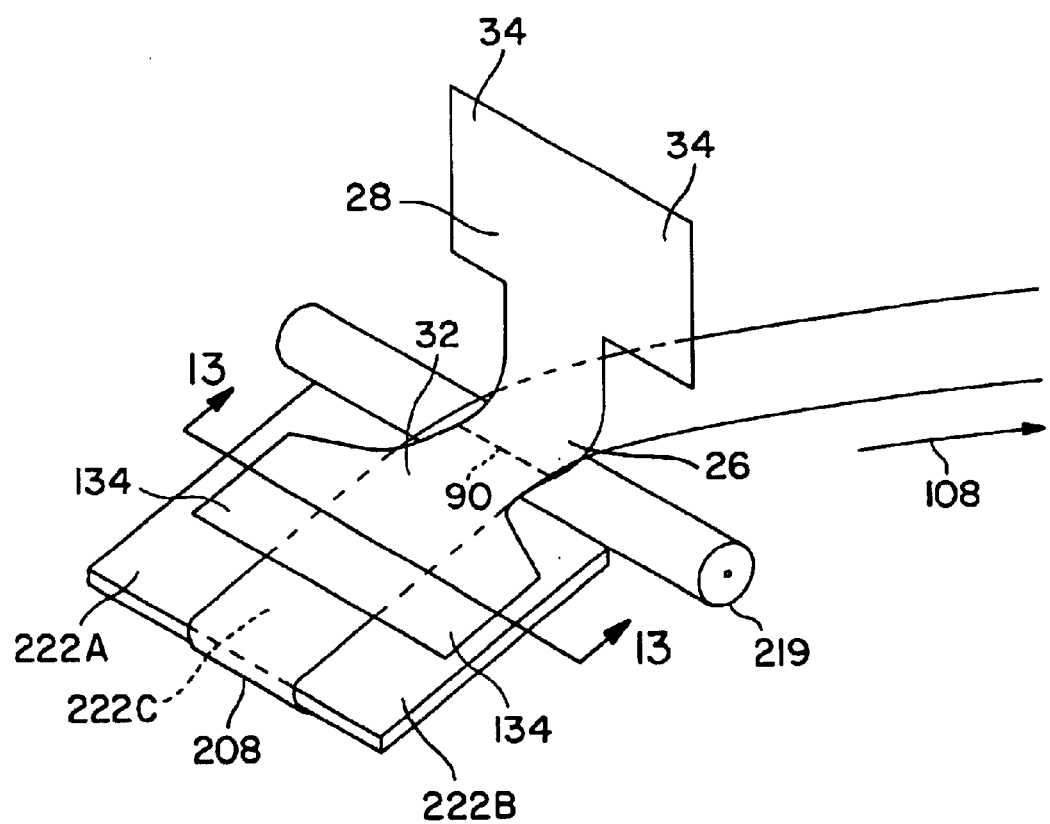
FIG. 12 is a front view of a garment on the channeled transfer plate and the lower folding conveyor.
Figure 13:
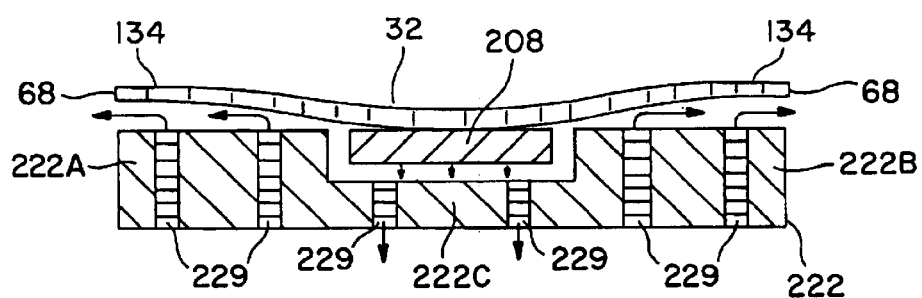
FIG. 13 is a cross-sectional view of FIG. 12 along line 13—13.

According to the invention, as shown in FIGS. 10–13, the transfer plate 222 is channeled and includes three regions, 222A, 222B and 222C. The channeled transfer plate allows the lower folding conveyor 208 to contact the garment 102 (FIGS. 12 and 13) in front of the folding nip 204 so that the chassis 32 stays properly aligned. Regions 222A and 222B of the transfer plate 222 support the side panels 134 while the lower folding conveyor 208 contacts and guides the chassis 32. The chassis 32 can be held by vacuum on the lower folding conveyor 208 (as illustrated in FIG. 13 by the downward facing arrows below the lower folding conveyor 208). The vacuum of the lower folding conveyor 208 helps to align the chassis as the garment 102 enters folding nip 204. Vacuum can be applied through holes 229 in region 222C of the transfer plate 222.

Regions 222A and 222B can also provide a layer of air to support the side panels 134 via holes 229. Compressed air can be applied through holes 229 in regions 222A and 222B. The air blows up and toward the distal edges 68 of the side panels 134 in the direction of the arrows on top of regions 222A and 222B in FIG. 13 so that the air also extends and straightens the side panels 134 fully from the chassis 32. As shown in FIGS. 12 and 13, the side panels 134 move over regions 222A and 222B simultaneous to the chassis 32 being held by vacuum on the lower folding conveyor 208.

With reference to FIG. 8, the folding mechanism 202 can include a pair of opposed tucker blades 240 that move in an orbital manner to pass through the vertical path of the garment 102. The tucker blades 240 can contact the crotch region 26 of the garment 102 and insert the crotch region into the folding nip 204. The folding mechanism 202 can alternatively draw the crotch region 26 of the garment into the folding nip 204 with vacuum. There are many suitable ways to initiate pushing or pulling the crotch region 26 into the folding nip 204, such as 360 degree rotating arms, reciprocating blades, conveyor belts with fingers, pivoting pins on a drum, cammed pins on a drum, or the like. As the crotch region 26 enters the folding nip 204, the leading half of the garment 102 reverses direction over the transfer plate 222 and is pulled into the folding nip 204. The vacuum puck 224 can cease drawing vacuum at this point to release the leading half. The vacuum in the product control drum 220 is released when the leading edge changes direction. Alternatively, high pressure air could be supplied by the product control drum 220 to urge the leading edge of garment 102 to transfer from the vacuum puck 224 to the transfer plate 222. Air flow could be directed as needed to maintain panel control during transfer. Correspondingly, the trailing half of the garment 102 is pulled around the upper nose roll 218. Thus, both halves of the garment 102 can change from motion in a generally vertical plane to motion between the folding conveyors 206 and 208 in a generally horizontal plane. Use of the terms "vertical" and "horizontal" are in relation to the drawings, however, the orientation of the folding mechanism 202 need not be the same as that illustrated in the drawings.

Figure 3:
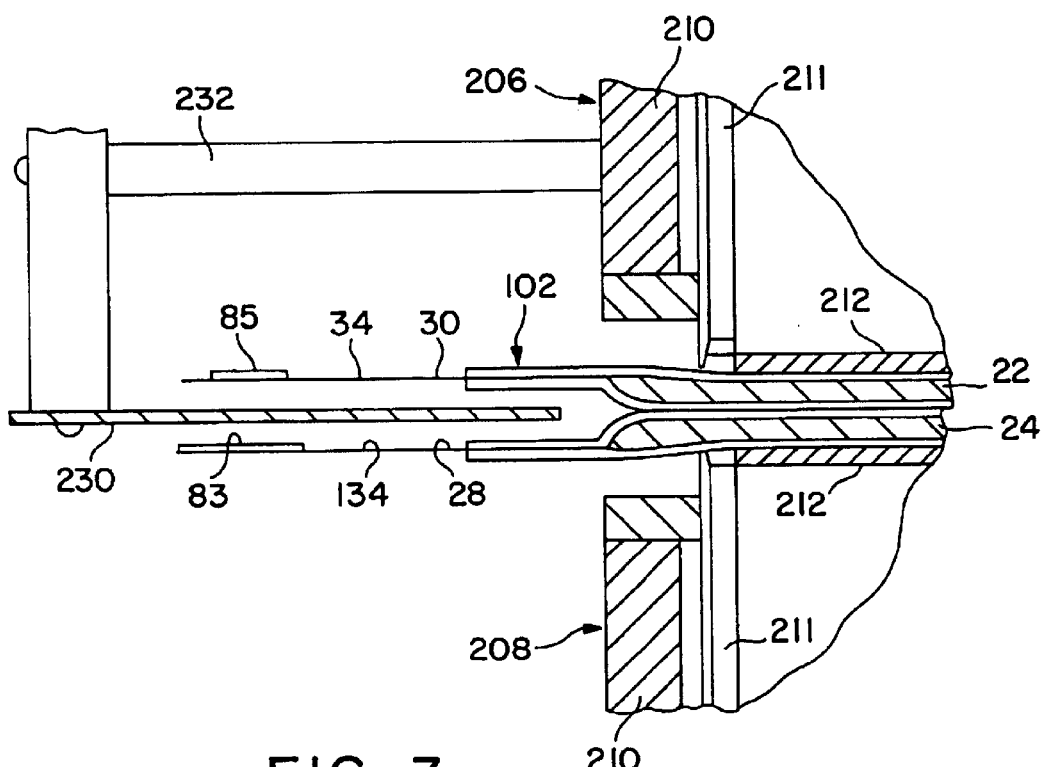
FIG. 3 illustrates an enlarged section view of a portion of a garment between the horizontal sections of upper and lower folding conveyors, following folding of the garment.

The illustrated folding mechanism 202 can maintain separation between the front and back side panels 34 and 134 from the time the crotch region 26 enters the folding nip 204 until the garments 102 are downstream of the folding nip (FIG. 3). As the garment 102 enters the folding nip 204, vacuum can be applied to the upper nose roll 218 so that the outstretched side panels 34 of the trailing half are drawn by vacuum to the upper nose roll 218. The trailing side panels 34 are thus drawn to the upper nose roll 218 and follow its rotation around the roll and over side panel separation members, which can be in the form of plates 230 (FIGS. 2 and 3) or other suitable shapes. Similarly, as the leading half of the garment 102 is pulled into the folding nip 204, vacuum can be applied to the lower nose roll 219 so that the outstretched side panels 134 of the leading half are drawn by vacuum to the lower nose roll 219. The leading side panels 134 are thus drawn to the lower nose roll 219 and follow its rotation around the roll and beneath the side panel separation plates 230. If vacuum is used to hold the side panels 34 on nose rolls 218 or 219, it is important that the vacuum can be turned off quickly to prepare for the leading panels of the next product. It is also important to be able to turn on the vacuum quickly and with high volumes of air to ensure drawing the side panels 134 to the nose rolls 218 and 219. The use of a high speed rotary vacuum valve in combination with this process can improve the machine speed and performance of this section. The cross machine direction length of the nose rolls 218 and 219 can be selected to enable the side panels to be drawn to the nose rolls as the side panels enter the folding nip 204. Alternatively, the side panels can be maintained separated from one another by drawing the leading side panels 134 toward a relatively wider vacuum folding conveyor 208 and drawing the trailing side panels 34 toward a relatively wider vacuum folding conveyor 206. Moreover, the nose rolls 218 and 219 could employ rough surfaces, static charges on the surfaces, air blasts, gravity or combinations thereof to maintain the side panels 34 and 134 separate from each other.

The illustrated separation plates 230 are generally interposed between the folding conveyors 206 and 208. The separation plates 230 are disposed on opposite sides of the machine center line and are disposed outward from the machine center line. As depicted in FIG. 2, the separation members 230 each have an upstream end located in proximity to the nose rolls 218 and 219 and an opposite downstream end located downstream of the nose rolls. In the illustrated embodiment, each upstream end can be straight, curved upward, downward or tapered, and each downstream end is positioned at the end of the horizontal run of the folding conveyors 206 and 208. The separation plate 230 can extend farther in the machine direction 108 to maintain separation between the front and back side panels 34 and 134 if desired.

The separation plate 230 can include a low friction material or coating, such as: stainless steel; Teflon; aluminum; ultra-high molecular weight polyethylene (UHMW-PE); polyoxymethylene (acetals), for instance a homopolymer available from E. I. Du Pont de Nemours and Company, Wilmington, Del. USA under the tradename DELRIN; or the like. In particular embodiments, the separation plate 230 can include a thin layer of teflon, UHMW-PE, DELRIN or the like bonded to a plate formed of steel, aluminum or the like. The separation plate 230 can be mounted using suitable support members 232 (FIG. 3) mounted to either of the folding conveyors 206 or 208 or other suitable frame structures (not shown). Separation plate 230 can also have an integral air blast built into it to aid in the stabilization and transport of the side panels 34 and 134 at high speeds.

The desired amount of spacing of the separation plates 230 will depend upon the size of the garments 102. For purposes of the present invention, the garments 102 will be said to define a minimum transverse width dimension and a maximum transverse width dimension. The minimum transverse width dimension is the narrowest portion of the garment 102, which can be in the crotch region 26, or +/−25% narrower than the crotch region 26. The maximum transverse width dimension can be the widest portion of the garment 102, which is typically in one of the waist regions 22 or 24. The separation members 230 are desirably spaced from one another in a cross machine direction a distance greater than the minimum transverse width dimension and less than the maximum transverse width dimension. Alternatively, the separation members 230 could be spaced from one another in a cross machine direction a distance less than the minimum transverse width dimension. For example, the separation members 230 could be tapered to push the nose of the product together for packaging effects or product presentation to other functions after this point. The distance can also be fixed but narrower than crotch region 26.

Sensing devices can also be employed to detect products that have folded side panels or that are misaligned. The garment side panels 34 and 134 are desirably outstretched in the cross machine direction (FIG. 3) throughout the folding process.

FIG. 3 illustrates a portion of a partially assembled garment 102 positioned between the upper and lower folding conveyors 206 and 208 at a location downstream of the nose rolls 218 and 219. At this point, the garment 102 has been folded in half and is being transported in the machine direction 108 by the conveyors 206 and 208. The front waist region 22 and front side panels 34 of the partially assembled garment 102 are disposed above the back waist region 24 and back side panels 134. The first fastening component 83 is disposed on the inner surface 28 of the back side panel 134 and the second fastening component 85 is disposed on the outer surface 30 of the front side panel 34. The outstretched side panels 134 of the leading half are positioned on one side of the separation plate 230 and the outstretched side panels 34 of the trailing half are positioned on an opposite side of the separation plate. The illustrated folding mechanism 202 can thus maintain the front side panels 34 separated from the back side panels 134 during folding.

Each folding conveyor 206 and 208 as illustrated in greater detail in FIG. 3 can include a frame structure 210, a plurality of rotatable pulleys 211 associated with the frame structure, and a continuous belt 212 carried on the pulleys. A drive system and conveyor shaft (not shown) can be used to rotatively drive one or more of the pulleys. The folding conveyors 206 and 208 can include vacuum conveyors as are well known in the art, in which case the continuous belt can be formed of a fluid permeable material. The folding conveyors desirably transport the garments 102 with the longitudinal center line of the training pants traveling on the longitudinal center line of the conveyors. As depicted, the front and back side panels 34 and 134 can project laterally outward from the frame structure 210, outstretched in the cross-machine direction.

From the folding station 200, the continuous stream of discrete, partially assembled and folded garment 102 can be processed through various finishing stations, for operations such as fastener engagement, side panel tucking, packaging, or the like. Any suitable method and apparatus can be used to engage the fastening components 82–85 to make a prefastened and refastenable product. Particular methods and apparatus for making prefastened products are disclosed in U.S. patent application Ser. No. 09/858,212, filed on May 15, 2001 (U.S. Publication US 2002/0005257, 17 Jan. 2002)

by C. R. Tomsovic et al. and titled "Method And Apparatus For Forming A Lap Seam"; U.S. patent application Ser. No. 09/855,451, filed on May 15, 2001 (U.S. Publication US 2002/0002358, 03 Jan. 2002) by D. H. Durrance et al. and titled "Presentation Of Fastening Components For Making Prefastened And Refastenable Pants"; U.S. patent application Ser. No. 09/858,071, filed on May 15, 2001 (U.S. Publication US 2002/0003024, 10 Jan. 2002) by B. R. Vogt et al. and titled "Garment Side Panel Conveyor System And Method"; U.S. patent application Ser. No. 09/855,334, filed on May 15, 2001 (U.S. Publication US 2002/0003022, 10 Jan. 2002) by J. G. Csida et al. and titled "Presentation And Bonding Of Garment Side Panels"; and U.S. patent application Ser. No. 09/855,951 filed on May 15, 2001 (U.S. Publication US 2002/0007773, 24 Jan. 2002) by L. C. Hietpas et al. and titled "Orbital Motion Device For Seaming Garments"; the disclosures of which are incorporated herein by reference.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of folding garments, comprising:
    creating a folding nip between first and second folding conveyors;
    transporting a plurality of discrete articles on the first folding conveyor toward the folding nip, each discrete article comprising a chassis and defining a leading half including opposed leading side panels, a trailing half including opposed trailing side panels, and an interconnecting region disposed between and interconnecting the leading and trailing halves;
    guiding the leading half onto a transfer plate using a product control drum having at least one vacuum puck, the at least one vacuum puck comprising multiple pieces;
    moving the interconnecting region into the folding nip; and
    advancing the leading and trailing halves into the folding nip.

2. The method of claim 1, wherein the leading half and the trailing half comprise mechanical fastening components.

3. The method of claim 1, wherein the at least one vacuum puck comprises at least three pieces.

4. The method of claim 3, wherein one of the at least three pieces supports the chassis and two of the at least three pieces support the opposed leading side panels of each discrete article.

5. The method of claim 1, further comprising engaging fastener components on the leading side panels and the trailing side panels of each discrete article.

6. The method of claim 1, wherein an amount of vacuum pulled by each of the multiple vacuum puck pieces is controlled separately.

7. The method of claim 1, further comprising providing at least one fluid stream to control the leading side panels while the leading half is over the transfer plate.

8. The method of claim 1, wherein guiding the leading half onto a transfer plate comprises supplying high pressure air.

9. A method of folding garments, comprising;
    creating a folding nip between first and second folding conveyors;
    transporting a plurality of discrete articles on the first folding conveyor toward the folding nip, each discrete article comprising a chassis and defining a leading half including opposed leading side panels, a trailing half including opposed trailing side panels, and an interconnecting region disposed between and interconnecting the leading and trailing halves, the leading half and the trailing half comprising mechanical fastening components;
    guiding the leading half onto a channeled transfer plate;
    moving the interconnecting region into the folding nip; and
    advancing the leading and trailing halves into the folding nip.

10. The method of claim 9, further comprising straightening the leading side panels prior to advancing the leading and trailing halves into the folding nip.

11. The method of claim 9, wherein the channeled transfer plate comprises at least three regions.

12. The method of claim 9, further comprising aligning each discrete article by contacting the discrete article with one of the folding conveyors in front of the folding nip.

13. The method of claim 12, further comprising simultaneously moving the leading side panels over the transfer plate.

14. The method of claim 12, further comprising holding the discrete article on the second folding conveyor by vacuum.

15. A method of folding garments, comprising:
    creating a folding nip between first and second folding conveyors;
    transporting a plurality of discrete articles on the first folding conveyor toward the folding nip, each discrete article comprising a chassis and defining a leading half including opposed leading side panels, a trailing half including opposed trailing side panels, and an interconnecting region disposed between and interconnecting the leading and trailing halves;
    guiding the leading half onto a transfer plate, the transfer plate providing a layer of air under the discrete articles;
    moving the interconnecting region into the folding nip;
    advancing the leading and trailing halves into the folding nip.

16. The method of claim 15, wherein the layer of air is provided by at least one of the group consisting of air jets, air bars, and air knives.

17. The method of claim 15, wherein the layer of air supports the leading side panels.

18. The method of claim 1, wherein the folding nip is formed by at least one timed vacuum roll.

19. The method of claim 18, wherein vacuum of the vacuum roll can be turned at least one of on and off quickly.

20. The method of claim 9, wherein the folding nip is formed by at least one timed vacuum roll.

21. The method of claim 20, wherein vacuum of the vacuum roll can be turned at least one of on and off quickly.

22. The method of claim 15, wherein the folding nip is formed by at least one timed vacuum roll.

23. The method of claim 22, wherein vacuum of the vacuum roll can be turned at least one of on and off quickly.

* * * * *